United States Patent
Spillert et al.

(10) Patent No.: US 6,514,766 B2
(45) Date of Patent: Feb. 4, 2003

(54) MODIFIED ERYTHROCYTE SEDIMENTATION RATE

(75) Inventors: Charles R. Spillert, 10 Edgemont Rd., West Orange, NJ (US) 07502; Marcelle Khalil, Morganville, NJ (US)

(73) Assignee: Charles R. Spillert, West Orange, NJ (US)

( * ) Notice: Subject to any disclaimer, the term of this patent is extended or adjusted under 35 U.S.C. 154(b) by 0 days.

(21) Appl. No.: 09/915,198

(22) Filed: Jul. 25, 2001

(65) Prior Publication Data

US 2002/0115222 A1 Aug. 22, 2002

Related U.S. Application Data

(60) Provisional application No. 60/221,464, filed on Jul. 26, 2000.

(51) Int. Cl.[7] ............................................. G01N 33/86
(52) U.S. Cl. .......................................... 436/70; 436/69
(58) Field of Search ...................................... 436/69, 70

(56) References Cited

U.S. PATENT DOCUMENTS

| | | | | |
|---|---|---|---|---|
| 5,506,145 | A | * | 4/1996 | Bull et al. ................... 210/782 |
| 5,783,447 | A | | 7/1998 | Spillert et al. |
| 5,792,660 | A | | 8/1998 | Spillert et al. |
| 5,888,826 | A | * | 3/1999 | Ostgaard et al. ............ 422/101 |
| 6,150,174 | A | * | 11/2000 | Sin et al. ...................... 422/73 |
| 6,245,573 | B1 | | 6/2001 | Spillert |
| 6,268,217 | B1 | * | 7/2001 | Barton et al. ................. 436/10 |
| 6,342,391 | B1 | * | 1/2002 | Chen et al. ............... 252/408.1 |
| 6,403,328 | B1 | * | 6/2002 | Clampitt ...................... 435/13 |

OTHER PUBLICATIONS

Bull, B.S. et al. J. Clin. Pathol. vol. 46: pp. 198–203 (1993).

* cited by examiner

*Primary Examiner*—Jill Warden
*Assistant Examiner*—Monique T. Cole
(74) *Attorney, Agent, or Firm*—Klauber & Jackson

(57) ABSTRACT

Methods for enhancing the value of the traditional erythrocyte sedimentation rate (ESR) test are provided by including an ESR-modifying agent, such as a metal ion, in the sample. Results of the resulting modified ESR are correlated with the health status of the animal.

22 Claims, No Drawings

MODIFIED ERYTHROCYTE SEDIMENTATION RATE

CROSS-REFERENCE TO RELATED APPLICATION

This application claims priority under 35 U.S.C. 119(e) to provisional application serial No. 60/221,464, filed Jul. 26, 2000, and is incorporated herein by reference in its entirety.

FIELD OF THE INVENTION

The invention relates to an improved whole-blood or isolated red blood cell diagnostic test for diagnosing or predicting various inflammatory and other conditions.

BACKGROUND OF THE INVENTION

Erythrocyte sedimentation rate (ESR) is a simple diagnostic test which determines the distance red blood cells in a sample of anticoagulated whole blood settle in one hour, and is expressed in units of mm per hour. This test measures the acute phase response to inflammatory disease. The current ESR test is similar to that described by Fahraeus (1921, The suspension-stability of the blood. Acta Med Scand 55:1–228) and Westergren (1921, Studies of the suspension stability of the blood in pulmonary tuberculosis. Acta Med Scand 54:247–282) in 1921, and has changed little since that time. The International Council for Standardization in Hematology (ICSH) has more recently put forth its description for the Erythrocyte Sedimentation Rate (ESR; Bull B S, Caswell M, Ernst E et al. ISCH recommendations for measurement of erythrocyte sedimentation rate. J Clin Path 1993, 46:198–203). The standardization method describes blood sample collection, anticoagulation, dilution of sample, sedimentation pipette and holding device specifications, calculating result and verification. The anticoagulant blood is drawn into a long tube with a narrow uniform bore. After placement of blood in the tube, the lower end is sealed, the tube placed in a vertical position and the distance (usually mm) the erythrocytes settle in 1 hour recorded as the ESR. Normal values are considered to be 15 mm or less. Automatically-zeroing ESR tubes are available as well as automatic instrumental determination of ESR values.

The ESR is a nonspecific marker of the inflammatory process and appears simplistic in concept. That is, cells and plasma interact under the influence of gravity and the final sedimentation distance of cells at one hour can be measured by simply reading the graduated tube. Beyond diagnosis of inflammatory diseases per se, reports describe the use of ESR in monitoring sickle cell disease, osteomyelitis, stroke, myocardial infarction, cancer, pregnancy, infection, atherosclerosis, rheumatoid arthritis, ischemic heart disease and trauma.

However, the major problems with the ESR are that it (1) is a nonspecific marker for disease; (2) it has lack of sensitivity in some disease states, and (3) it is rarely elevated in asymptomatic individuals, who may have occult disease. It is towards improving the value and utility of the ESR test and increasing its sensitivity for the diagnosis, monitoring and prognostication of various conditions and diseases that the present invention is directed.

The citation of any reference herein should not be construed as an admission that such reference is available as "Prior Art" to the instant application.

SUMMARY OF THE INVENTION

In its broadest aspect, the present invention is directed to a method for determining the health status of an animal, preferably a human, by carrying out the sequential steps of: (i) obtaining an anticoagulated sample of whole blood from the animal; (ii) determining at least one erythrocyte sedimentation rate (ESR) of the sample in the presence of at least one ESR-modulating agent; and (iii) correlating the at least one ESR in the presence of the at least one ESR-modulating agent with the health status of the animal. The health status may indicate presence or extent of a condition or disease, propensity for the development of a condition or disease, or effect of therapy on a condition or disease, such as, but not limited to, inflammation, sickle cell disease, osteomyelitis, stroke, myocardial infarction, cancer, pregnancy, infection, atherosclerosis, rheumatoid arthritis, ischemic heart disease and trauma. It may also help decide on the course of therapy of a particular disease or condition, such as whether the cardiac patient is a candidate for an angioplastic procedure or will need a more invasive surgery such as a bypass operation.

The foregoing modified ESR determination may also be performed in combination with at least one other assay, such as but not limited to clotting time or a metal- or polymer-modified clotting time, to provide data of additional diagnostic or prognostic utility. Other additional tests include red blood cell deformability and any other clotting parameter, as traditionally done or as modified by the addition to the blood sample of a modifying agent such as a metal ion, polymer, or other agent as described herein.

By way of non-limiting examples, the ESR-modulating agent may be a metal ion, such as silver, mercuric or lanthanum ion; a polymer, such as methylcellulose or polyvinylpyrrolidone; epinephrine; an oxidant such as hydrogen peroxide; a procoagulant such as but not limited to a snake venom, such as Russell's viper venom; an endotoxin; or collagen.

In a further embodiment, the above method may be carried out with an additional ESR determination is performed on the sample in the absence of an ESR-modulating agent. In another embodiment, an additional ESR determination is made on the sample in the presence of a second ESR-modulating agent. All of the foregoing methods may be performed on washed erythrocytes (red blood cells) rather than anticoagulated whole blood. They may be washed or isolated in plasma, albumin solution, normal saline, etc.

The anticoagulated sample of whole blood may be anticoagulated with, for example, citrate, isocitrate, heparin or EDTA.

The prognostic value of the present invention includes, among other uses, determining from a sample of blood whether a cardiac patient will be a candidate for an angioplastic procedure, or may need more extensive surgery such as a bypass operation. This may be achieved from the modified ESR determination, optionally in combination with at least one additional determination, such as a modified clotting time. In one embodiment, a whole blood sample is drawn, anticoagulated, and a modulator such as a silver (I) or mercury (II) salt, or a polymer such as methyl cellulose, is added to the sample. The sample is divided into two aliquots. With one aliquot, a gravity erythrocyte sedimentation rate is determined. With the other sample, a calcium salt is added and the clotting time is determined. From the results of the modified ESR and modified clotting time, prognosis as to the likelihood or risk of acute or chronic coronary heart disease may be made. In a patient presenting with acute chest pain, the test aids in determining whether an angioplastic procedure may be useful or whether the patient should be prepared for a coronary artery bypass graft procedure.

Therefore, it is an object of the invention to improve the diagnostic specificity of an erythrocyte sedimentation rate (ESR) determination by performing the ESR determination in the presence of an ESR-modulating agent, optionally along with at least one additional whole blood test.

These and other aspects of the present invention will be better appreciated by reference to the following Detailed Description.

DETAILED DESCRIPTION OF THE INVENTION

Improvements have been made herein in the methodology of performing the erythrocyte sedimentation rate (ESR) so that many of its defects can be removed, and moreover its sensitivity may be increased to expand its diagnostic and prognostic value. The test is extremely simple to perform, and can be done on an anticoagulated whole blood sample present in a capillary or other similar tube, wherever a source of gravity is present. While instruments can help automate the determination and perhaps increase the speed of the test (from the usual prescribed one hour of settling), the basic test is applicable to a wide variety of conditions and locations, including medical facilities with minimal equipment and personnel, military or battlefield conditions, as well as in space. Alternate gravity conditions will of course require recalibrating the ESR, but the improvements described herein are applicable to the ESR test wherever and however it is normally performed. The various aspects of the invention applicable to human blood are equally applicable to the blood of non-human animals, such as domesticated animals, wild animals, and animals raised for food and other products.

The main aspect of the invention is the surprising and unanticipated finding that the addition of various agents to the blood sample alters the value of the ESR and moreover, the ESR value of the blood with the addition of the agent or agents (hereinafter referred to as the "modified ESR") is of improved diagnostic value in identifying abnormalities, i.e., samples from individuals with a condition or disease, and furthermore, the magnitude of the severity of the condition or disease. The modified ESR also permits more sensitive monitoring of conditions during their early, occult or covert stages, at stages where no other detection method is useful, during progression or treatment, as well as permitting the early identification of conditions or disease which have not yet manifest in the form of symptom or syndrome, or exhibiting an altered traditional ESR value. The modified ESR can be used to rule in or rule out certain conditions or diseases. It can also help guide the course of treatment. Thus, the modified ESR improves upon all of the uses of the traditional ESR test.

The improvements provided by the instant invention are manifold. It is great boon in countries of lower economic capabilities, where diagnostic facilities have limited personnel and equipment. It can be performed by lesser trained laboratory staff or others. It is a great aid in the in-vitro and in-vivo testing of drugs and therapies. It is a prognostic indicator for surgical, pharmaceutical or other modes of disease treatment or prevention. It can be performed simply in remote locations, such as in polar field stations or during space travel, to monitor health status and gain an early indication of need for medical intervention.

In addition, the modified ESR test described here may be performed in conjunction with other tests on whole blood, perhaps as simple as the ESR test, to increase the diagnostic and prognostic value of the modified ESR test. For example, a calcium-activated clotting time (recalcification time) can also be performed on the same anticoagulated blood sample. Any whole blood coagulation instrument may be used to perform the at least one additional test, such as may be performed using a Sonoclot Coagulation Analyzer, Thrombelastograph, Hemocron 801, Sigma KC4A, Diagnostica Stago ST4, or any other related instrument. As noted above the at least one other whole blood test may be performed as generally and traditionally done in the hematology test setting, or it may be a modified test such as a metal-ion- or polymer-modified whole blood test, such as a modified clotting test described in U.S. Pat. Nos. 6,245,573; 5,792,660; and 5,783,447, to name but a few non-limiting examples where additional reagents are added to a traditional hematologic test to obtain additional and useful data that may be diagnostic or prognostic as to a disease or condition.

By way of non-limiting example, a method for the manual determination of the modified ESR may be carried out as follows. To 900 microliters of human citrated (or isocitrate, EDTA, heparin or other anticoagulant) whole blood (CWB) in a plastic vial was added 100 microliters of test vehicle or test reagent dissolved in vehicle. The samples are capped, incubated at 37 degrees Celsius for 10 minutes and then the samples were added to sedimentation rate tubes and the ESR determined at varying time intervals. The ESR is defined as the distance traveled by the erythrocytes (red blood cells under the influence of [1× g] gravity). Unless noted otherwise, the ESR values reported are those determined at the traditional time, one hour.

As described herein, various reagents may be added to the anticoagulated whole blood sample to provide the modified ESR determination. Numerous such reagents in several classes have been found to alter ESR and provide diagnostically-useful information. These agents generally include (1) metal ions, such as but not limited to silver, mercuric and lanthanum ion; (2) polymers, such as but not limited to methylcellulose and polyvinylpyrrolidone; (3) epinephrine; (4) oxidants, such as but not limited to hydrogen peroxide; (5) a procoagulant agent such as a snake venom, such as but not limited to Russell's Viper Venom; (6) endotoxins, such as but not limited to Gram-positive endotoxin and Gram-negative endotoxin (LPS); and (6) collagen; to name but a few examples of such compounds. Each of these groups will be elaborated on in more detail below. Criteria for the selection of such reagents may include one or more of the following: toxic to cells; membrane altering; alters solvent properties; reacts with protein, lipids, DNA, or RNA; cellular or plasma distorter, e.g., pH, ionic strength, viscosity, alter electrostatic or other factor to potentiate cellular interactions or inhibit same; and generate more or less effective cellular collisions, cellular adhesion, lysis; and generate, or prevent generation of above-type compounds.

The preferred modulator of ESR rate is a metal ion, such as silver (I), mercury (II), lanthanum (III); lead (II), cadmium (II), tin (I), iron (III), copper (II), cobalt (II), nickel (II), zinc (II), cerium (III), magnesium (II), calcium (II), chromium (II), lutetium (III), scandium (III), thallium (III), ytterbium (III), thorium (IV), and uranate (II). Silver (I) and mercury (II) are preferred. These may be included in the anticoagulated whole blood at level of about up to mM concentrations. Methylcellulose (MC) may be included at about 0.1%.

Other agents include polymers, such as but not limited to methylcellulose and polyvinylpyrrolidone; epinephrin (ADRENALINE®); oxidants, such as but not limited to hydrogen peroxide; snake venoms, such as procoagulant snake venoms including but not limited to Russell's Viper Venom; endotoxins, such as but not limited to Gram-positive endotoxin and Gram-negative endotoxin (LPS); and collagen. Others include tissue factor, prothrombotic venoms, thrombin, platelet activating factor, fibrinogen, kaolin, celite, adenosine diphosphate, arachidonic acid, collagen, and ristocetin. Factors with anticoagulant activity useful as modulators of the clotting process of the present invention include protein C, protein S, antithrombin III, thrombomodulin, tissue plasminogen activator, urokinase, streptokinase, and Von Willebrand Factor. Addition of therapeutic drugs which may modulate the coagulant activity of blood may also be used as modulators in the present invention. In addition, cancer cell extracts and amniotic fluid may be used.

As will be seen in the examples below, the prognostic value of a combination of the modified ESR and modified clotting time is useful in determining whether a cardiac patient presenting with severe chest pain is a candidate for an angioplastic procedure, such as balloon angioplasty, or upon catheterization prove to have disease too advanced for angioplasty and would therefore be a candidate for CABG or other procedure. Significant time, health care costs, and importantly, morbidity and mortality could be reduced if such a determination could be made and the appropriate procedure performed immediately. The present modified ESR test, optionally in combination with a modified clotting time, serves this function.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE I

Reproducibility of Methods

The differential ESR and spontaneous hematocrit values were determined using eight samples of human citrated whole blood (CWB), divided into 4 aliquots: A. Control; B. Heparin (1 unit/ml); C. Heparinase (1 unit/ml); and D. B+C above. All values throughout herein are expressed as mean±standard deviation. The ESR and spontaneous hematocrit were as follows:

| Method | A | B | C | D |
|---|---|---|---|---|
| ESR (mm/hr) | 78.4 ± 4 | 78.3 ± 51 | 79.0 ± 50 | 78 ± 50 |
| Hematocrit (% RBC) | 57.6 ± 23 | 58.9 ± 22 | 57.6 ± 23 | 59.3 ± 25 |

There was no significant differences in values obtained for ESR aliquots or hematocrit aliquots. These data show that the test substance did not alter experimental values and there was no change in mean values or standard deviations within groups.

In this study no changes in ESR were in agreement with the lack of change observed in gravity-hematocrits.

EXAMPLE II

Effect of silver ion (Ag(I), 0.005%) mercuric ion (Hg(II), 0.005%) and methylcellulose (MC, 0.1%) on the ESR values of bloods with normal (<20), moderately elevated (20–50) and highly elevated (>50) ESR values. Bloods with normal (<20), moderately elevated (20–50) and highly elevated (>50) ESR values were studies by modified ESR using silver (I), mercury (II) and methylcellulose at the indicated final concentrations. The results are as follows.

| Group (n) | Control | Ag(I) | Hg(II) | MC |
|---|---|---|---|---|
| normal (7) | 5.4 ± 5.6 | 3.1 ± 4.2* | 5.9 ± 4.9 | 75 ± 4.1** |
| moderate elevation (5) | 38.2 ± 8.2 | 16.4 ± 18.9* | 26.6 ± 12.5 | 113 ± 21** |
| highly | 105.6 ± 22.0 | 30.6 ± 24.4** | 50.4 ± 27.8** | 128.6 ± 10.5* |

*$p < 0.05$;
**$p < .01$ compared to control values

The above data shows that silver (I) ion reduces ESR when compared to control value for normal, moderately elevated and highly elevated control ESR values; and that mercury (II) ion is similar to silver (I) ion except that there is no difference for normal control ESR values. Methylcellulose increases the ESR compared to control value for all groups of ESR values.

By use of these and similar reactants, a differential diagnosis based upon changes of ESR values dependent upon diseases, stages of disease, therapy, etc., may be demonstrated.

EXAMPLE III

Comparison of ESR Values of Apparently Healthy Individuals and Patients

The ESR values of seven apparently healthy and eight patients were evaluated as control (saline), MC and Ag$^+$. There was significant differences in each value when compared by an unpaired t-list.

|  | Healthy (n = 8) | Patients (n = 7) |
|---|---|---|
| ESR control | 6.3 ± 3.7 | 23.9 ± 5 |
| ESR MC | 78.0 ± 23 | 110.6 ± 20 |
| ESR Ag$^+$ | 0.3 ± 0.5 | 5.9 ± 7 |

$P < 0.05$ in each pair, unpaired t-test

EXAMPLE IV

Effect of ESR-Altering substances on Gravity-Hematocrit

It has been shown that MC generally increased ESR values whereas Ag$^+$ and Hg$^{2+}$ generally decrease ESR values when compared to an inert control. The following samples were studies by "gravity hematocrits," i.e., the bloods were allowed to settle at ambient gravity for 24 hours, and the % red blood cells measured from the interface between the settled red blood cells and the plasma.

| Gravity-Hematocrits | | | |
|---|---|---|---|
| Control | MC | Ag$^+$ | Hg$^{2+}$ |
| 40.6 ± 1 | 32.4 ± 8* | | |
| 37.0 ± 12 | | 52.8 ± 18** | 55.3 ± 15** |

*p < 0.05 compared to control; n = 8
**p < 0.001 compared to control value; n = 6

Comparison of ratios of centrifuged compared to gravity-hematocrits may be a useful clinical or experimental parameter. It may be that a reagent that increases ESR may decrease spontaneous gravity hematocrit and one that decreases ESR may increase gravity hematocrit. All possible variations may result in useful clinical or experimental parameters.

EXAMPLE V

Effect of Epinephrine on ESR

The ESR for the treated blood (1 microgram/ml ADRENALINE®) was 49.3±17 and control 54.0±29 (p=NS). Although no significant difference, in 1 of 3 samples employed a 27% increase was observed. Epinephrine may be used in some clinical states.

EXAMPLE VI

Effect of hydrogen peroxide on ESR

Hydrogen peroxide at concentrations of 1 mM is known to decrease erythrocyte deformability. This is similar to changes that occur to these cells in trauma and in surgical patients. The ESR for control and peroxide-treated samples (n=3) are 49.3±17.0 and 68.7±34 mm/hr, respectively. (P=0.24,NS). However, in one sample the ESR increased by greater than 60% when treated with peroxide. This reagent may be useful in evaluating ESR to improve clinical decision-making in some disease states (e.g., those with oxidative stress like trauma, surgery etc.).

EXAMPLE VII

Effect of Snake Venom on ESR Values

Russell's viper venom (RVV), a snake venom, has been shown to induce sphero-echinocytosis in human erythrocytes. Whether this change in cell morphology can be monitored by ESR changes was studied. Three samples of CWB were treated with (50 ng/ml) RVV and ESR values determined. Control ESR was 49.3±17 and RVV-treated 57.3"30 (p=0.43, NS).

Although there was no significant change, in one case the ESR increased by 33%. As in other examples some diseases or clinical states may respond to treatment in vitro and with some agents and others may not.

EXAMPLE VIII

ESR values for patients being treated for cardiac diseases (n=6) Blood samples from patients being treated for cardiac diseases were evaluated by modified ESR in accordance with the methods described herein. The results are as follows.

| Control | MC | Ag$^+$ | Hg$^{2+}$ |
|---|---|---|---|
| 50.3 ± 49 | 91.1 ± 43*** | 8.4 ± 9** | 28.3 ± 28* |

*p < 0.05;
**p < 0.01;
***p < 0.0001

The ESR values determined with MC are significantly greater than control values whereas the Ag$^+$ and Hg$^{2+}$ values are reduced.

The large standard deviation (SD) is due, in part, to a broad and varied clinical state (e.g. cardiogenic shock, heart failure, heart attack, infections etc.). However, modified-ESR values may be helpful in clinical decision making by ruling in/ruling out a variety of possibilities. This may markedly reduce costs by negating additional expensive testing or procedures and focusing on techniques to rapidly obtain more effective treatment to patients.

EXAMPLE IX

Effect of Lanthanum Chloride, Polyvinylpyrrolidone 40 (PVP-40) and Methyl Cellulose (MC) on ESR and Spontaneously Settled Hematocrit Lanthanum chloride (LC) 0.1%, polyvinylpyrrolidone 40, (PVP-40) 0.1% and methylcellulose 0.1% were used as ESR-modifying agents.

| Reagent | ESR (n = 8) |
|---|---|
| Control | 41.3 ± 35 |
| Lanthanum chloride | 40.9 ± 36 |
| PVP-40 | 56.4 ± 47 |
| MC | 117 ± 21* |

*p < 0.05 when compared to control

All MC ESR values are greater than aliquot control value. However, with PVP, 3 of 8 (38%) are reduced compared to control. Therefore, it is apparent that not all polymers alter ESR in same manner (e.g. PVP and MC); and that PVP and other test reagents may be useful in some clinical states although mean values may show no significant change but individual patient values may be relevant.

Hematocrits of above samples allowed to spontaneously settle (ca. 18 hours).

| Treatment | Hematocrit (% RBC) |
|---|---|
| Control | 40.6 ± 14 |
| PVP-40 | 34.0 ± 9* |
| LC | 45.0 ± 13 |
| MC | 32.4 ± 8* |

*p < 0.05 compared to control value

EXAMPLE X

Effect of Endotoxin (LPS) and Mercuric Ion ($Hg^{2+}$) on ESR

|  | Control | $Hg^{2+}$ 0.005% | LPS 10 µg/ml | $Hg^{2+}$ + LPS 0.005%, 10 µg/m |
|---|---|---|---|---|
| 30 min. | 75 | 0 | 50 | 13 |
| 60 min. | 99 | 5 | 92 | 26 |

LPS reduces ESR at both time intervals comparted to control. $Hg^{2+}$ reduces value compared to LPS or control. $Hg^{2+}$ plus LPS is greater than $Hg^{2+}$ but less than LPS. The relative ratios or individual values may vary with disease, prognosis, etc.

EXAMPLE XI

Data for isolated, washed RBC. RBC suspended in either 5% albumin or 5% albumin 0.1% MC.

| ESR | | |
|---|---|---|
| 5% Albumin | 5% Albumin + MC | 5% Albumin + 0.005% $Ag^+$ |
| 11 | 130 | 6 |
| 16 | 135 | 8 |
| 18 | 130 | 7 |

Silver ion reduces the ESR and MC increases same if the cells are resuspended in albumin, a purified protein isolated from plasma.

When same cells suspended in the same type "O" human plasma the following ESR values were obtained.

| ESR (mm) | | |
|---|---|---|
| plasma | Plasma + MC | Plasma + $Ag^+$ |
| 0 | 35 | 0 |
| 0 | 22 | 0 |

The ESR in plasma is reduced compared to albumin. However, MC treated cells have elevated ESR compared to compared to control.

EXAMPLE XII

A study was undertaken to compare the results of the modified ESR with a concurrently-performed clotting time in the presence or absence of a metal (as such as silver (I) or mercury (II). In addition, comparison was made to red blood cell (RBC) deformability measured using a LORCA ektactyometer, which monitors RBC deformability as a function of low-shear deformability. RBCs that have low deformability are more prone to block the microvasculature because of their inability to deform during transit through capillary vessels treatment of RBCs with peroxides increases the rigidity of cells and alters their membrane characteristics.

Patients undergoing invasive cardiac procedures have RBCs that are abnormal in their ability to deform at lower shear values (i.e., are too rigid). This in part may explain abnormal ESR and even perhaps altered coagulation changes.

RBC deformability is expressed in the form of an Elongation Index (EI), which, at 37° C. and a shear of 0.30 Pa for normal blood, is about 0.064 (n=8 patients). The greater the value of EI, the greater the deformability. Eight cardiac patients evaluated for EI showed a mean EI of 0.02±0.019.

EXAMPLE XIII

The control and modified ESR was performed on hospital medical patients (medical) in the surgical intensive care unit (SICI) and the cardiac care unit (ccu), with the following results.

| | ESR (gravity) in mm (mean ± S.D.) | | |
|---|---|---|---|
| Patient Group | Control | Ag+ | MC |
| Medical (n = 13) | 21 ± 16 | 1.1 ± 2.2 | 42 ± 19 |
| SICU (n = 12) | 43 ± 25* | 9.5 ± 13* | 63 ± 18* |
| CCU (n = 8) | 45 ± 24* | 7.0 ± 12* | 57 ± 14* |

*Significantly different from corresponding medical patient group.

While the SICU and CCU patients show only a doubling of the control ESR values, the modified, silver ESR were about 9 and 7 times normal, respectively.

EXAMPLE XIV

Prior to cardiac catheterization, patients with severe chest pain intended for at least an angiology procedure, and possible balloon angioplasty (if indicators from the angiology assessment were favorable), were evaluated for clotting time and ESR. Clotting time was performed without or with various modulators as described in U.S. Pat. No. 6,245,573. ESR was performed without or with silver (I), mercury (II) or methylcellulose (MC). In addition, the thromoelastograph (TEG) alpha value was determined which indicates the rate of fibrin clot formation. A normal alpha value is in the range of 36 to 48 degrees. Of the 13 patients studied, three were candidates for balloon angioplasty. The bloods were collected just after cannulization and prior to catheterization.

| | Angiology patients that were not candidates for an angioplasty (n = 10) | Angiology patients that were then angioplastied (n = 3) |
|---|---|---|
| Clotting time in seconds control | 287 ± 40 | 337 ± 57 |
| +silver (I) | 130 ± 22 | 70 ± 55* |
| +mercury (II) | 213 ± 57 | 242 ± 80 |
| +methycellulose | 261 ± 30 | 276 ± 34 |
| TEG Rate (alpha) control | 66 ± 4.6 | 59 ± 11 |
| +silver (I) | 68 ± 5.6 | 68 ± 8.0 |
| +mercury (II) | 40 ± 8.2 | 37 ± 10 |
| +methylcellulose | 67 ± 4.7 | 62 ± 10 |
| ESR (mm) control | 33 ± 21 | 43 ± 27 |
| +silver (I) | 4.0 ± 4.2 | 19 ± 21* |
| +mercury (II) | 4.7 ± 7.7 | 6.7 ± 12 |
| +methylcellulose | 43 ± 19 | 60 ± 20 |

*p < 0.05 compared to value in other column

The three angioplasty candidates presented with acute coronary disease which was treatable with the balloon procedure. As seen in the above table, a sample of blood prior to assessing the patient's candidacy for angioplasty indicated a more normal clotting time (normal range 450–690 seconds) but a significantly lower silver-modified clotting time and not as much of a decreased silver ESR as the patients who were not candidates for angioplasty. These patients had disease of a more chronic nature and were candidates for coronary artery bypass grafts (CABG) or other treatment modalities.

Thus, the combination of a higher clotting time, reduced silver modified clotting time and an only modestly reduced silver ESR is predictive for a potential candidate for angioplasty. In contrast, a lower clotting time that is not as responsive to silver, and a greatly reduced silver ESR is predictive of potential non-candidacy for angioplasty and an alternate procedure to address a chronic disease.

EXAMPLE XV

The effect of the IIb/IIIa platelet inhibitor REOPRO (abciximab) was evaluated on modified ESR as described herein. The silver ESR value of a sample of normal blood was 3.6±3.1 mm. With REOPRO, the value was 7.4±8.4. (Significantly different, p=0.013).

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A method for determining the candidacy of a mammal for coronary artery angioplasty comprising the sequential steps of:
    i) obtaining an anticoagulated sample of whole blood from said mammal;
    ii) determining at least one erythrocyte sedimentation rate (ESR) of said sample in the presence of at least one ESR-modulating agent; and
    iii) correlating said at least one ESR in the presence of said at least one ESR-modulating agent with the candidacy of a mammal for coronary artery angioplasty.

2. The method of claim 1 wherein said ESR-modulating agent is a metal ion.

3. The method of claim 2 wherein said metal ion is selected from the group of silver, mercuric and lanthanum ion.

4. The method of claim 1 wherein said ESR-modulating agent is a polymer.

5. The method of claim 4 wherein said polymer is selected from the group consisting of methylcellulose and polyvinylpyrrolidone.

6. The method of claim 1 wherein said ESR-modulating agent is epinephrine.

7. The method of claim 1 wherein said ESR-modulating agent is an oxidant.

8. The method of claim 7 wherein said oxidant is hydrogen peroxide.

9. The method of claim 1 wherein said ESR-modulating agent is a procoagulant agent.

10. The method of claim 9 wherein said procoagulant agent is a snake venom.

11. The method of claim 10 wherein said snake venom is Russell's viper venom.

12. The method of claim 1 wherein said ESR-modulating agent is an endotoxin.

13. The method of claim 1 wherein said ESR-modulating agent is collagen.

14. The method of claim 1 wherein an additional ESR determination is performed on said sample, said ESR determined in the absence of an ESR-modulating agent.

15. The method of claim 1 wherein an additional ESR determination is made on said sample, said additional ESR determined in the presence of a second ESR-modulating agent.

16. The method of claim 1 wherein said anticoagulated sample of whole blood is anticoagulated with an anticoagulant selected from the group consisting of citrate, isocitrate, heparin and EDTA.

17. The method of claim 1 wherein said ESR is performed on washed erythrocytes from said sample.

18. The method of claim 1 wherein said ESR is a gravity hematocrit.

19. A method for determining the health status of a mammal comprising carrying out the method of claim 1 in combination with at least one further hematological test.

20. The method of claim 19 wherein said at least one further hematological test is a clotting time determination or a red blood cell deformability determination.

21. The method of claim 20 wherein said at least one further hematological test is a clotting time determination.

22. The method of claim 21 wherein said clotting time is a metal-ion-modified or polymer-modified clotting time.

* * * * *